(12) United States Patent
Langlois et al.

(10) Patent No.: US 8,033,172 B2
(45) Date of Patent: Oct. 11, 2011

(54) HAND-HELD FLAW DETECTOR IMAGING APPARATUS

(75) Inventors: Pierre Langlois, Quebec (CA);
Agostino Abatte, Boxborough, MA (US); Josefina R. Quiles, legal representative, Boxborough, MA (US)

(73) Assignee: Olympus NDT, Waltham, MA (US)

( * ) Notice: Subject to any disclaimer, the term of this patent is extended or adjusted under 35 U.S.C. 154(b) by 665 days.

(21) Appl. No.: 12/176,642

(22) Filed: Jul. 21, 2008

(65) Prior Publication Data
US 2008/0314153 A1    Dec. 25, 2008

Related U.S. Application Data

(63) Continuation-in-part of application No. 11/332,912, filed on Jan. 17, 2006, now abandoned.

(60) Provisional application No. 60/643,628, filed on Jan. 14, 2005.

(51) Int. Cl.
*G01N 29/04* (2006.01)
(52) U.S. Cl. ........................................... 73/626
(58) Field of Classification Search ............ 73/625, 73/626
See application file for complete search history.

(56) References Cited

U.S. PATENT DOCUMENTS
4,127,034 A * 11/1978 Lederman et al. ............. 73/626
* cited by examiner

*Primary Examiner* — John Chapman, Jr.
(74) *Attorney, Agent, or Firm* — Ostrolenk Faber LLP

(57) ABSTRACT

The present invention relates to a flaw detector imaging apparatus for detecting and visualizing a flaw in a target material to be investigated, comprising an ultrasonic phase-array probe comprising an array of ultrasonic transducers and a flaw detector. The flaw detector includes at least one trigger channel to trigger ultrasonic emitting transducers of the array at respective time delays to produce an ultrasonic beam propagating through the target material, and a single receiver channel to receive echo signals produced by ultrasonic receiving transducers of the array in response to ultrasonic wave echoes reflected from a flaw in the target material. The single receiver channel comprises a delay circuit imparting to the received echo signals the respective time delays as used in the triggering of the ultrasonic emitting transducers and a combiner of the delayed echo signals. A processor is responsive to the echo signals produced by the ultrasonic receiving transducers, received by the single receiver channel and time delayed by the delay circuit to produce an image of the flaw from which the ultrasonic wave echoes are reflected. A display connected to the ultrasonic processor displays the image of the flaw.

10 Claims, 15 Drawing Sheets

HAND-HELD FLAW DETECTOR IMAGING APPARATUS

CROSS-REFERENCE TO RELATED APPLICATIONS

The application is a continuation-in-part application of U.S. patent application Ser. No. 11/332,912 filed on Jan. 17, 2006 entitled A HAND-HELD FLAW DETECTOR IMAGING APPARATUS, the entire disclosure of which is included herein by reference.

FIELD OF THE INVENTION

The present invention relates to ultrasonic non-destructive testing of structures and materials.

BACKGROUND OF THE INVENTION

Typical ultrasonic flaw detectors are similar to oscilloscopes, and generally incorporate special features designed to help detecting and characterizing flaws in materials. Flaw detectors are widely used for material evaluation and they are designed as small, hand-held microprocessor-based devices suitable for both laboratory and industrial applications. A schematic block diagram of a typical ultrasonic flaw detector is illustrated in FIG. 1.

A typical, conventional flaw detector uses one channel pulse generator to excite an ultrasonic transducer and create sound waves (traveling mechanical vibration) propagating through the inspected material. Reflected echoes (energy) from the boundaries and/or flaws are converted by the ultrasonic transducer into electrical signals which are amplified, and sent to a receiver channel. The electrical signals are then digitized, filtered and displayed on a screen as ultrasonic waveforms (A-scans) that can be interpreted by the operator. Alarm gates (amplitude thresholds) are often employed to monitor signal levels at selected points in the A-Scan to flag echoes from flaws.

The conventional ultrasonic flaw detector technology is reliable and well accepted; it is also relatively simple to use, particularly for slightly oriented, accessible and relatively big flaws. Straight and angled beam testing is generally employed to find flaws. In many instances, however, simple display of A-Scans is cumbersome and difficult to interpret. Moreover, conventional hand-held flaw detectors do not offer imaging capabilities for flaw visualization and are typically limited to a single ultrasonic transducer. Since beam orientation is necessary for accurate flaw detection, conventional flaw detectors also use a series of angle wedges to cover a small range of beam orientated inspection.

With such a typical flaw detection configuration, it is not possible to visualize and adequately characterize small volumetric flaws. It is also more complex to reach flaws in hidden regions and visualize them at the same time. One way to produce real-time flaw visualization without moving the transducer in time-consuming raster scan pattern is to use echographic images based on phase-array technology using an array or matrix of ultrasonic transducers.

Ultrasonic phase-array probes generate focused beams by controlling the time delays of the excited ultrasonic waves which in turn are generated from a plurality of separate and spaced apart ultrasonic transducers such as piezoelectric elements. Beam focusing and steering is also achieved by phase-array probes at the reception of the returned echoes by applying the same control delay(s) as for the emission. These delays have a specific profile called focal law profile. Therefore, the ultrasonic beams can be focused and/or steered within a volumetric working space to probe for flaws and discontinuities in the material propagating the ultrasonic waves. Flaws in the body of material can be detected on the basis of ultrasonic echoes that are returned or deflected from such flaws. As phase-array beams are generated electronically, electronic raster scanning permits very rapid structural flaw imaging, flaw detection and volumetric characterization. Electronic raster scanning also allows to circumvent problems associated with a fixed mechanical lens of transducers, to eliminate all moving transducer parts, and to avoid many problems related to ultrasonic coupling.

Phase-array probes can create simple echographic sectorial scans (S-Scans) representation where multiple A-Scan signals with different angles are stacked and presented as a global electronic scan image. S-Scan can represent a color coded 2-D layout of the tested structure. It provides quick information since it gives the true depth representation and 2-D representation of the flaws.

Phase-array ultrasonic technology moved from the medical field to the industrial sector at the beginning of the 1980s. By the mid-1980s, piezocomposite materials were developed and made available to manufacture complex-shaped phase-array probes. The company R/D Tech Inc., whose address is 505, boul. du Parc-Technologique, Québec, Québec, Canada, G1P 4S9 has widely investigated and implemented the phase-array concept for industrial standardization and transfer of the technology. Phase-array development at R/D Tech Inc., has been based upon a series of portable phase-array instruments that can be operated in the field by a single operator, and collect data from engineering structures for remote analyses.

A need still exists for a hand-held, lightweight, portable flaw detection device that can be easily used to detect defects in materials and, then, to rapidly visualize these defects on a display, for example a LCD display, for better characterization, and in which simple display software algorithms can be used to locate and categorize the detected defects.

SUMMARY OF THE INVENTION

Therefore, the present invention relates to a flaw detector imaging apparatus for detecting and visualizing a flaw in a target material to be investigated, comprising:

an ultrasonic phase-array probe comprising an array of ultrasonic transducers;

a flaw detector including:
at least one trigger channel to trigger ultrasonic emitting transducers of the array at respective time delays to produce an ultrasonic beam propagating through the target material;
a single receiver channel to receive echo signals produced by ultrasonic receiving transducers of the array in response to ultrasonic wave echoes reflected from a flaw in the target material, the single receiver channel comprising a delay circuit imparting to the received echo signals the respective time delays as used in the triggering of the ultrasonic emitting transducers and a combiner of the delayed, received echo signals; and
a processor of the combined echo signals from the single receiver channel to produce an image of the flaw from which the ultrasonic wave echoes are reflected; and
a display connected to the ultrasonic processor to display the image of the flaw.

The present disclosure is also directed to a method of ultrasonic inspection for use with an ultrasonic imaging system comprising a pulse generating array including a plurality of transducer elements and a plurality of receiver channels, the method comprising: coupling a first group of elements of the array to the receiver channels; energizing the first group of said array according to a set of focal laws; processing echo signals sensed by said first group of transducer elements through said receiver channels; obtaining a respective digitized value representative for each of said echo signals; summing said digitized values into an accumulator; coupling a second group of transducer elements of said array to said receiver channels; energizing said array and obtaining a respective digitized value for the second group; summing the respective digitized values of the second group in said accumulator; and repeating said process steps to provide a cumulative sum value for a predetermined number of groups of the transducer elements of said array.

Preferably, in the above method, the number of elements in the first group equal the number of receiver channels. Also, the number of elements in the second group equals the number of elements in the first group. Still further, the processing may be carried out for a sufficient number of the groups to include all of the transducer elements in the array. The accumulator may comprise a memory block containing a previously stored value and a summing block which sums the digitized values with previously stored values and loads new values resulting from the summation operation into the memory block.

The foregoing and other objects, advantages and features of the present invention will become more apparent upon reading of the following non restrictive description of illustrative embodiments, given for the purpose of illustration only with reference to the appended.

DETAILED DESCRIPTION OF THE ILLUSTRATIVE EMBODIMENTS

Figure 1:
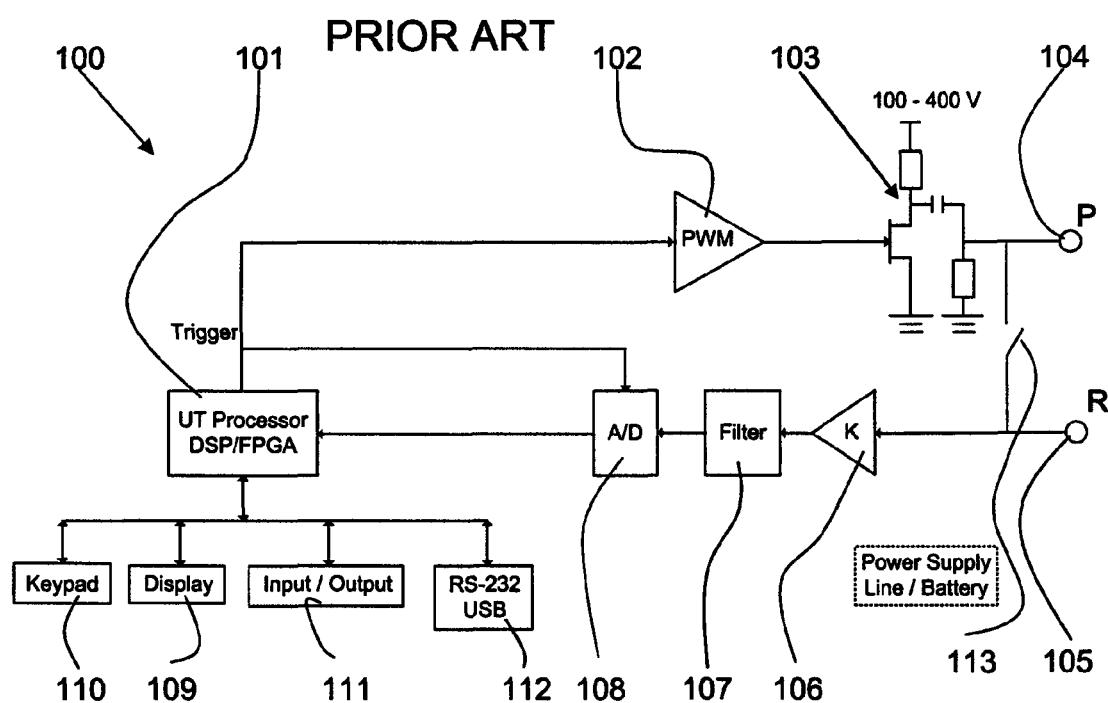
FIG. 1 is a schematic block diagram of typical ultrasonic flaw detector.

Non-restrictive illustrative embodiments of the flaw detector imaging apparatus and method according to the present invention will now be described. These non-restrictive illustrative embodiments are intended only to demonstrate the principle of the invention as well as the manner in which it can be implemented, and not to limit the scope of the present invention.

Non-restrictive general features of the flaw detector imaging apparatus and method in accordance with the present invention will first be described. Then, non-restrictive illustrative embodiments will be described with reference to the appended drawings.

According to these non-restrictive illustrative embodiments, the flaw detector imaging apparatus can be a hand-held apparatus intended to detect flaws, especially but not exclusively in engineering materials and/or structures (hereinafter referred to as target material to be investigated), such as metals, plastics and composites. The hand-held flaw detector imaging apparatus may comprises a flaw detector and an ultrasonic phase-array probe connected to the flaw detector through an ultrasonic cable. The phase-array probe may comprise an array of ultrasonic transducers to provide ultrasonic imaging capabilities without moving the ultrasonic transducers but by focusing and/or steering the ultrasonic beam from the probe to scan the target material to be investigated. The image of the flaw(s) can be displayed on an integrated display in real-time and can be created by the flaw detector by processing the ultrasonic echoes received by the probe and reflected from a tested region of the investigated material.

The phase-array probe with its array of ultrasonic transducers can be applied at a single point to produce real-time S-Scan imaging of flaws or can be moved along a surface of the material or structure to be investigated to create a complete image or cross sectional representation of the inspected target material (B-Scan representation).

The flaw detector may comprise a plurality of trigger channels to produce transducer-driving signals, and a plurality of receiver channels for receiving echo signals from the ultrasonic transducers. Real-time S-Scan images can be created by electronic scanning using phase-array ultrasonic beams with a pre-programmed sequence of phase-array law delay profiles (delay values associated with the ultrasonic transducers and used to focus the ultrasonic beam at a certain depth and/or steer this ultrasonic beam at several angles in the target material being investigated). For each focal law profile, a number n of trigger channels can be used to excite a number n of respective ultrasonic transducers of the phase-array probe.

For a compact design of the hand-held flaw detector imaging apparatus, a single receiver channel configuration can be used. In this case, a multiplexer can be used to receive the echo signals from the ultrasonic transducers, and a FIFO memory can be added to stack the multiplexed received signals before a summing stage. This compact design not only simplifies the architecture of the hand-held flaw detector imaging apparatus but also reduce power consumption and the manufacturing cost. This configuration also provides for high speed S-Scan imaging capabilities and real-time visualization of flaws in the tested materials. To form the S-Scan image of the inspected target material using the above described compact configuration, the ultrasonic transducers of the phase-array probe, for example n piezoelectric elements, can be excited by the trigger channels at n respective trigger times, and at each separate trigger times, only one ultrasonic echo is collected by the receiver channel.

As described in the foregoing description, the hand-held flaw detector imaging apparatus may comprise an ultrasonic phase-array probe including n spaced apart ultrasonic transducers, for example piezoelectric elements, used to produce ultrasonic beams propagated through the inspected material. Each ultrasonic beam can be focused and/or steered to achieve proper flaw imaging by applying appropriate law delay profiles on the ultrasonic transducers. Since the law delay profiles at the receiver channel are compensated for, additional delays can be added to the law delay profiles calculated for the trigger channels during excitation of the n transducers of the phase-array probe.

The hand-held flaw detector imaging apparatus and method can detect echoes produced by successive, different focused and/or steered beams incident on and reflected from a suspected flaw to produce simple S-Scan representation of the tested material. This is called the "pulse-echo" mode of inspection. The hand-held flaw detector imaging apparatus and method can also be operated using the well-known "pitch-catch" mode of inspection.

The ultrasonic phase-array probe may include an electronic circuit used to store characteristics of the transducer array and law delay profiles.

Non-restrictive illustrative embodiments of the flaw detector imaging apparatus and method according to the present invention will now be described in detail with reference to the accompanying drawings.

FIG. 1 is a schematic block diagram of the structure of a typical single channel ultrasonic flaw detector 100. The ultrasonic flaw detector 100 comprises an ultrasonic processor 101 responsible for system synchronization, signal processing and real-time display of the received echo signals.

The ultrasonic processor 101 produces synchronized pulses with a pre-programmed width. The synchronized pulses with pre-programmed width are processed through a pulse width modulator 102 and then amplified by a high power pulse amplifier 103 prior to being supplied to an ultrasonic transducer (not shown) connected to the trigger output 104 for example through an ultrasonic cable (not shown). The function of the ultrasonic transducer is to create an ultrasonic wave propagating through the target material to be inspected (ultrasonic emitting transducer).

Ultrasonic echoes reflected from boundaries and/or flaws in the target material are detected by the ultrasonic transducer connected to the receiver input 105 (ultrasonic receiving transducer). Just a word to mention that the same ultrasonic transducer or different ultrasonic transducers can be connected to the output 104 and input 105. More specifically, the ultrasonic emitting transducer and the ultrasonic receiving transducer can be the same ultrasonic transducer or different ultrasonic transducers. Depending on the configuration of the connections and the operation of the hand-held flaw detector imaging apparatus 100, a switch 113 can be actuated to interconnect or disconnect the output 104 and input 105 as required. Switch 113 can be operated manually or through the ultrasonic processor 101 as required.

Figure 2:
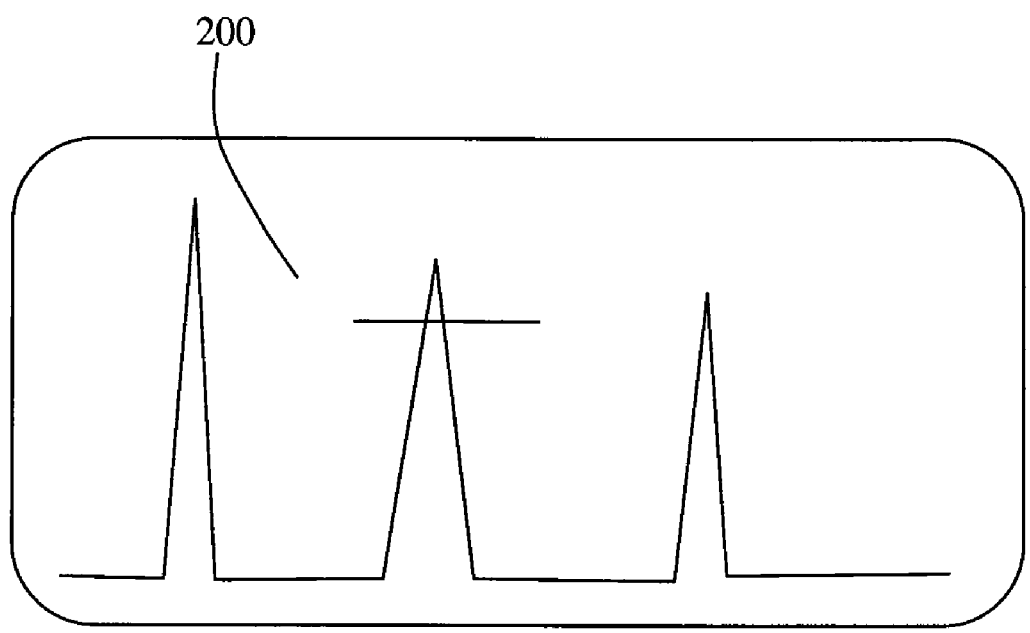
FIG. 2 is a graph showing A-Scan signals from a conventional flaw detector used to flag echoes from suspected flaws.

The reflected ultrasonic echoes are converted by the ultrasonic transducer into electric signals that are amplified by an amplifier 106, filtered in accordance with techniques well known to those of ordinary skill in the art through a filter 107 to remove parasitic or unwanted signal components, and then digitized through an analog-to-digital converter 108. Finally, the digitized signals are processed (if necessary) through the ultrasonic processor 101 for display onto a display unit 109. The reflected, digitized and processed signals can be displayed on the unit 109 under the form of an ultrasonic A-Scan waveform that can be interpreted by the operator to flag echoes such as 200 from suspected flaws as illustrated in FIG. 2.

The ultrasonic processor 101 can also be associated, for example, to a conventional keypad 110, input/output peripherals and/or ports 111 and a RS-232 USB port 112.

Figure 3:
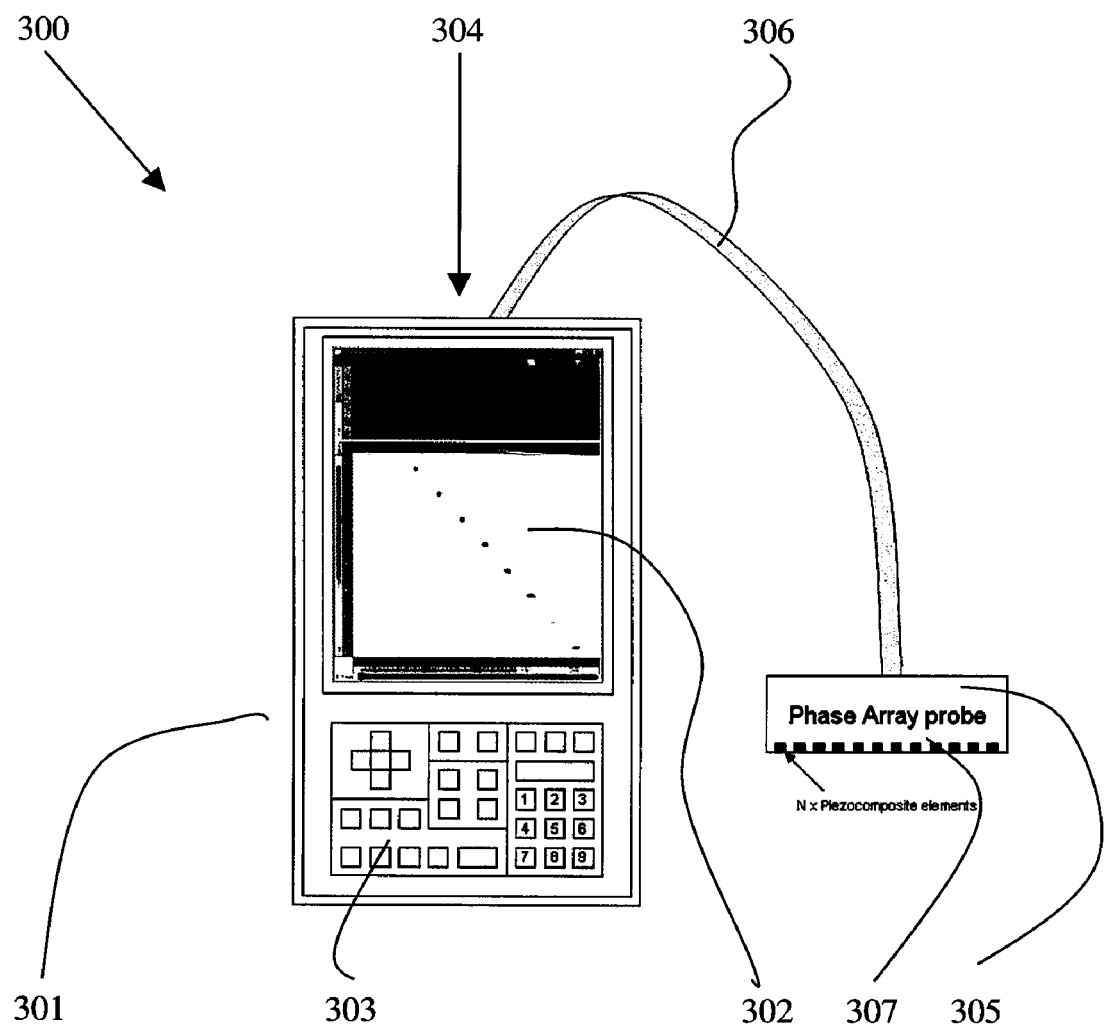
FIG. 3 is a schematic pictorial view of a hand-held flaw detector imaging apparatus in accordance with an illustrative embodiment of the present invention.

FIG. 3 is a schematic pictorial view of the hand-held flaw detector imaging apparatus 300 in accordance with a non-restrictive illustrative embodiment of the present invention. The hand-held flaw detector imaging apparatus 300 includes a battery powered advanced flaw detector 301 with integrated display 302, for example a LCD display, keyboard 303 and input/output peripheral and/or port 304. An ultrasonic phase-array probe 305 comprising an array of ultrasonic transducers 307, for example piezoelectric elements or any other suitable ultrasonic transducers, is connected to the input/output peripheral and/or port 304 through an ultrasonic cable 306. The flaw detector 301 produces ultrasonic S-Scan imaging of materials and flaws displayed on the integrated display 302 in real-time. This ultrasonic S-Scan imaging of materials and flaws is created through the flaw detector 301 by processing the received ultrasonic echoes reflected from the tested region of the target material and detected through the ultrasonic phase-array probe 305.

Figure 4:
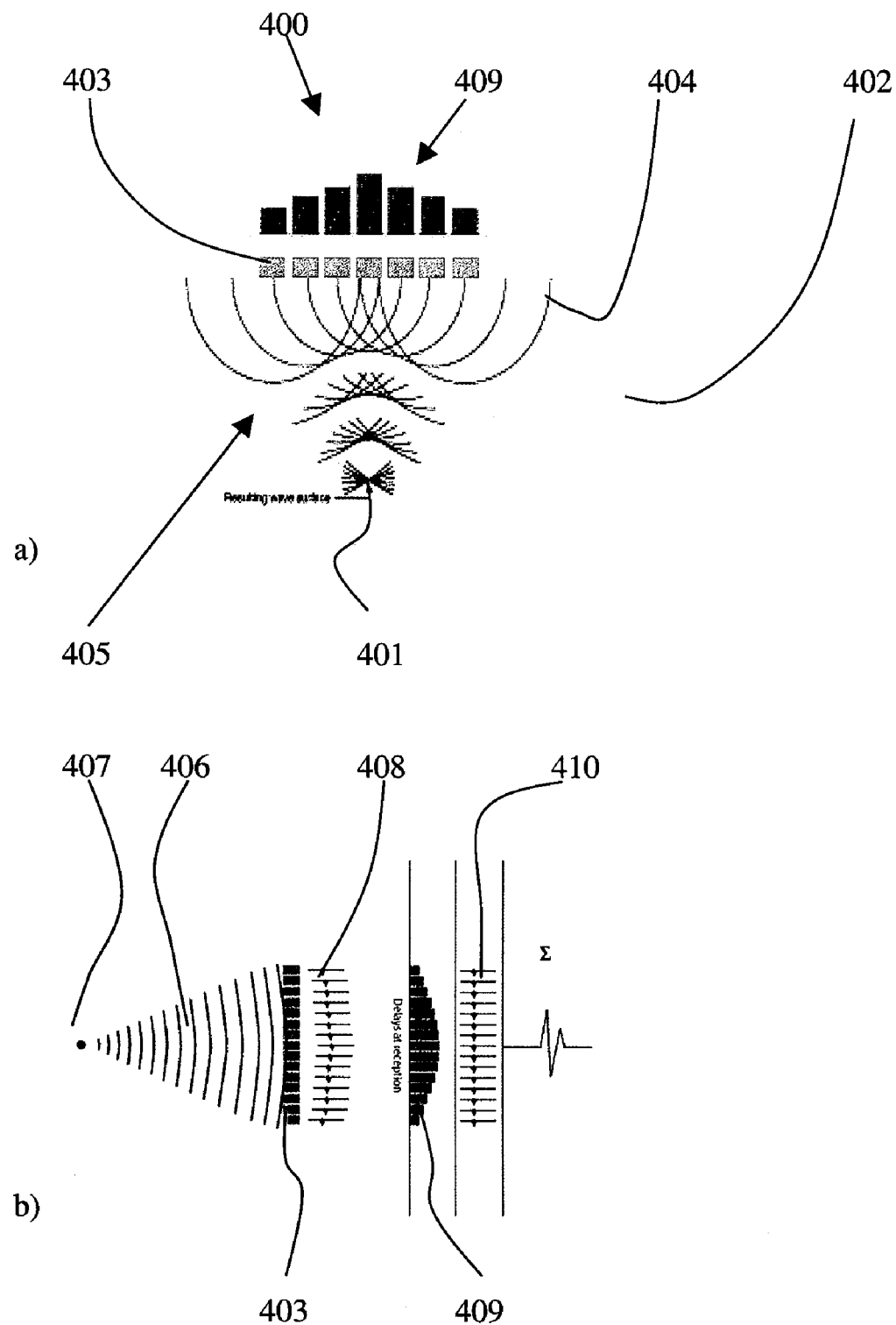
FIG. 4a is a schematic diagram illustrating electronic focusing of an ultrasonic beam using delays determined by a focal law profile during excitation of an ultrasonic phase-array probe.
FIG. 4b is a schematic diagram illustrating electronic focusing of an ultrasonic beam using delays determined by a focal law profile during reception of echoes from a flaw in an body of material under inspection.
Figure 5:
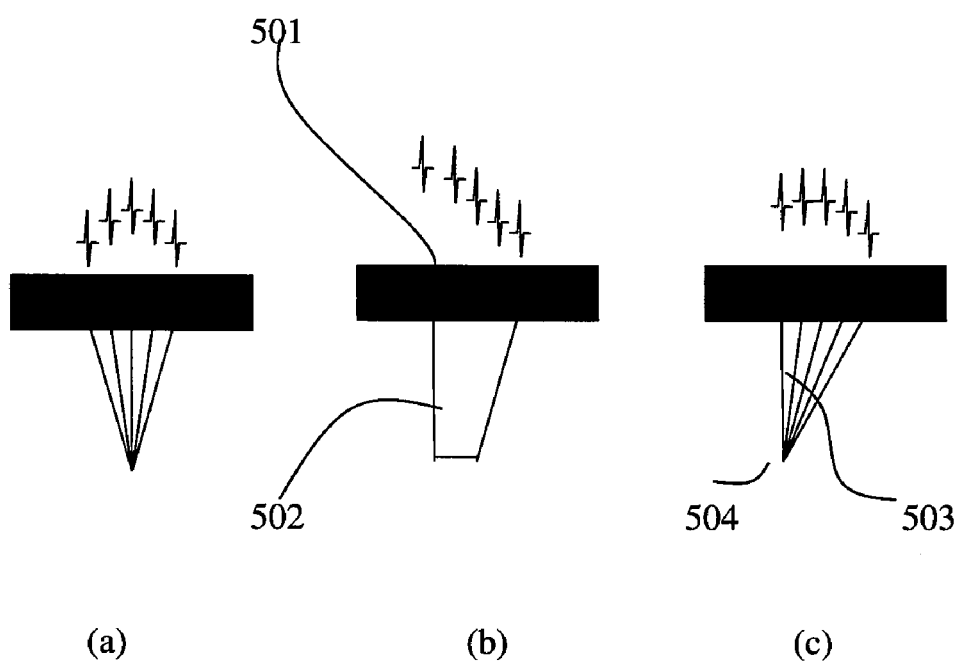
FIG. 5a is a schematic diagram illustrating an example of electronic beam focusing.
FIG. 5b is a schematic diagram illustrating an example of electronic beam steering.
FIG. 5c is a schematic diagram illustrating an example of electronic beam focusing and steering.

As illustrated in FIG. 4a, beam focusing with a phase-array probe including multiple ultrasonic transducers such as 403, for example piezoelectric elements, is obtained by emission through the multiple transducers 403 at predetermined time delays. For example, to focus at a point such as 401 of a body 402 of material to be investigated, the various transducers 403 are triggered at individually calculated time delays such as 409 taking into consideration the known velocity of propagation of the ultrasonic waves through the medium (target material 402). More specifically, the time delays 409 associated to the various transducers such as 403 are individually calculated so that the pressure fields such as 404 from the various transducers such as 403 reach the desired location (point of focus 401) in phase and at the same time. Such manipulation enables dynamic focusing and steering of the ultrasonic beam 405 at one or more locations simultaneously. FIG. 5a also illustrates the concept of beam focusing.

Referring now to FIG. 5b, beam steering with a phase-array probe including multiple ultrasonic transducers such as 501, for example piezoelectric elements, is also obtained by emission through the multiple transducers 501 at predetermined time delays. More specifically, the various transducers 501 are triggered at individually calculated time delays so that the resulting ultrasonic beam 502 propagates in the desired angular direction.

FIG. 5c illustrates the case in which the ultrasonic beam 503 is both steered to the left and focused at point 504.

Figure 6:
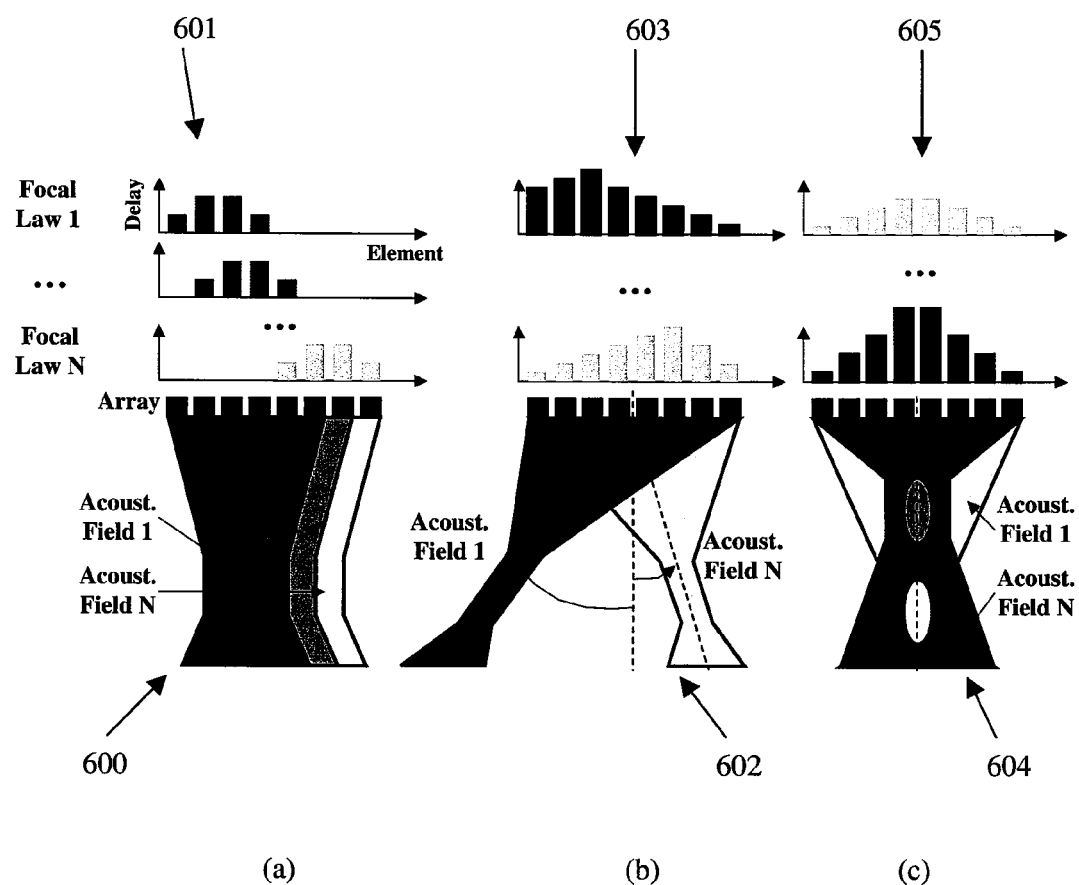
FIG. 6a is a schematic diagram illustrating an example of configuration for linear scanning using a phase-array probe.
FIG. 6b is a schematic diagram illustrating an example of configuration for sectorial scanning using a phase-array probe.
FIG. 6c is a schematic diagram illustrating an example of configuration for depth focusing a phase-array probe.
Figure 7:
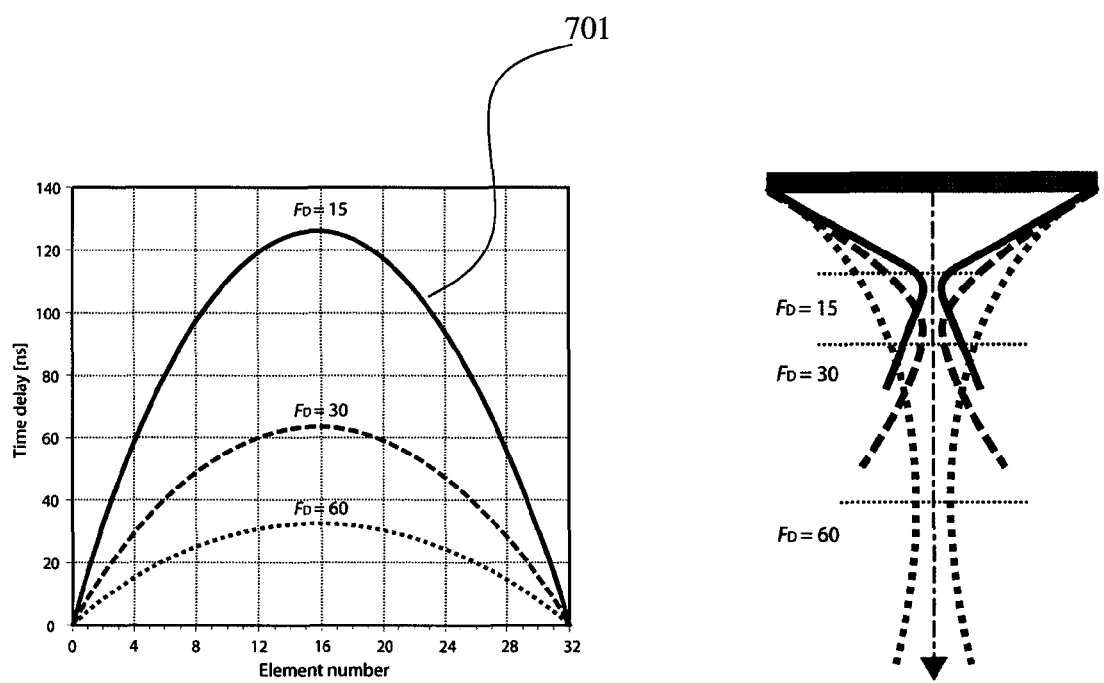
FIG. 7 is a graph illustrating focal law delay profiles and a schematic diagram showing the corresponding depth focusing distance for a 32-transducer linear array probe focusing at depths of 15 mm, 30 mm and 60 mm.

As illustrated in FIGS. 6a-6c, focusing and/or steering is achieved by applying pre-calculated law delay profiles as illustrated in FIG. 7. More specifically, FIG. 7 shows a graph (left) illustrating examples of focal law delay profiles such as 701 and a schematic diagram (right) showing the corresponding depth focusing distances (15 mm, 30 mm and 60 mm) for a 32-transducer linear array probe.

Referring to FIG. 6a, linear scanning 600 can be conducted by applying a pre-programmed sequence 601 of focal law delay profiles. In the same manner, FIG. 6b illustrates sectorial scanning 602 conducted by applying a pre-programmed sequence 603 of law delay profiles. Referring to FIG. 6c, depth focusing 604 can be conducted by applying a pre-programmed sequence 605 of focal law delay profiles.

Referring to FIG. 4b, ultrasonic wave echoes such as 406 reflected from, for example, a flaw 407 are detected by the transducers 403 to form echo signals 408. These signals are delayed by the same time delays 409 as in FIG. 4a to produce corresponding signals 410. The signals 410 and the time delays between these signals 410 are finally analysed to detect the flaw 407 and determine the exact position of this flaw.

Figure 8:
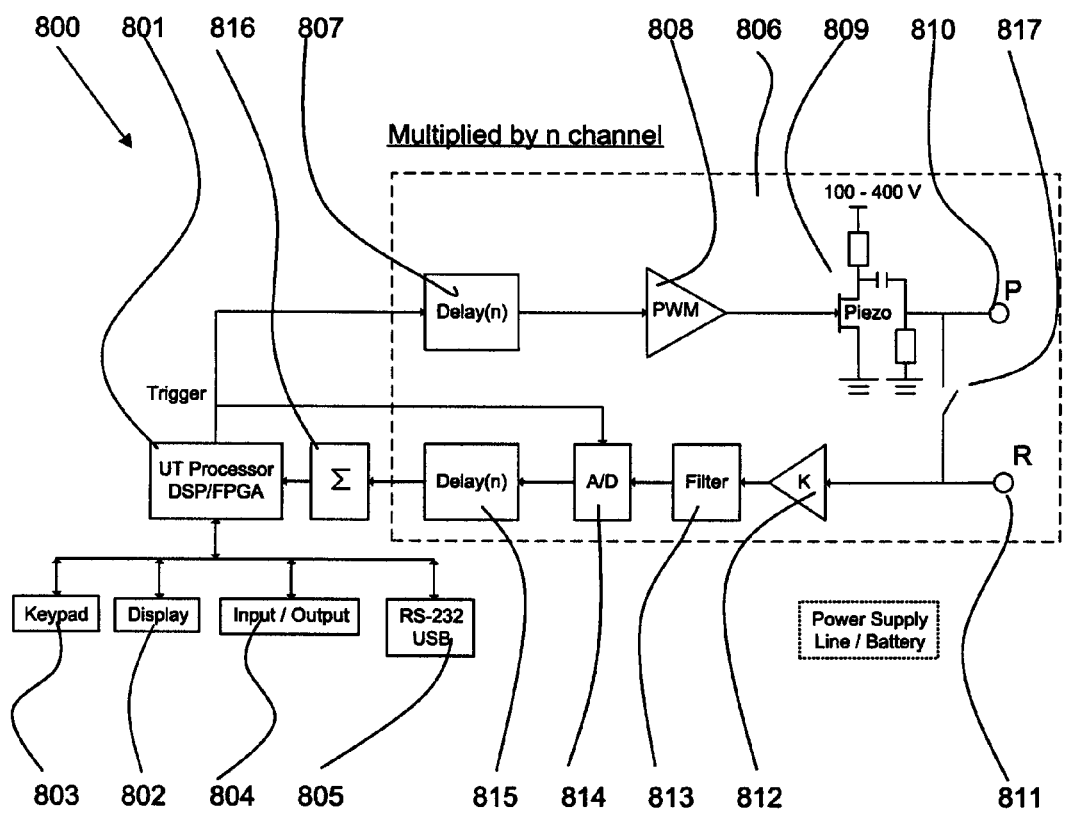
FIG. 8 is a block diagram of a non-restrictive, illustrative embodiment of the flaw detector imaging apparatus according to the present invention.

FIG. 8 is a block diagram of a non-restrictive illustrative embodiment 800 of the hand-held flaw detector 301 of FIG. 3. As shown in FIG. 8, the hand-held flaw detector imaging apparatus 800 comprises an ultrasonic processor 801 associated with a display unit 802, for example a LCD (Liquid Crystal Display) display, and conventional keypad 803, input/output peripherals and/or ports 804 and RS-232 USB port 805.

The ultrasonic processor 801 is responsible for system synchronization, signal processing and real-time displaying of the received signals.

The ultrasonic processor 801 produces synchronized pulses with a pre-programmed width. The synchronized pulses with pre-programmed width are processed through a number of n identical and parallel channels such as 806 respectively associated to the various transducers 307 (FIG. 3), such as piezoelectric elements, of the ultrasonic phase-array probe 305. Obviously, the number n of trigger channels 806 is equal to the number of transducers 307 and each channel 806 is associated to a respective one of the transducers 307 for driving and receiving signals from this transducer.

The synchronized pulses with pre-programmed width are supplied to a delay circuit 807 of each channel 806. The function of the delay circuit 807 is to delay the pulses from the ultrasonic processor 801 in order to supply to the corresponding transducer 307 the pulse with a delay corresponding to the delay associated to this transducer in the corresponding, pre-calculated law delay profile such as shown at 601, 603 and 605 in FIGS. 6a-6c.

The delayed pulses from delay circuit 807 are processed through a pulse width modulator 808 for adjusting the width of the pulse as required or desired, and then amplified by a high power pulse amplifier 809 prior to being supplied to the corresponding ultrasonic transducer 307 (FIG. 3) connected at the trigger output 810 through the ultrasonic cable 306. As described in the foregoing description, the function of the ultrasonic transducer 307 is to create a sound wave propagating through the target material to be investigated.

Ultrasonic echoes reflected from boundaries and/or flaws in the target material are detected by the ultrasonic transducer 307 connected to the receiver input 811. Just a word to mention that the same ultrasonic transducer 307 or different ultrasonic transducers 307 can be connected to the output 810 and input 811. More specifically, the ultrasonic emitting transducer and the ultrasonic receiving transducer can be the same ultrasonic transducer or different ultrasonic transducers. Depending on the configuration of the connections and the operation of the hand-held flaw detector 800, a switch 817 can be actuated to interconnect or disconnect the output 810 and input 811 as required. Switch 817 can be operated manually or through the ultrasonic processor 801 as required.

The reflected ultrasonic echoes are converted by the ultrasonic transducer 307 into electrical echo signals that are amplified by an amplifier 812, filtered in accordance with techniques well known to those of ordinary skill in the art through a filter 813 to remove parasitic or unwanted signal components, and then digitized through an analog-to-digital converter 814. The digitized signals from the converter 814 are then delayed through a delay circuit 815 through the same law delay profile as applied by delay circuit 807. A combiner 816 combines, for example sums the digitized and delayed signals from all the channels 806, and the digitized and delayed signals are processed (if necessary) through the DSP of the ultrasonic processor 801 and stacked to form the S-Scan image displayed on the display unit 802 for interpretation. The display can be a liquid crystal display (LCD) calibrated in units of time, depth or distance. Multi-color LCD displays can also be used to provide interpretive assistance. Since the reflected, digitized, delayed, summed and processed signals are displayed on the unit 802 under the form of a real-time S-Scan image display instead of only displaying the A-Scan signals, the flaws and their positions can be easily identified on the display unit 802.

Finally the S-Scan images can be stored through the input/output port 804 or through the USB port 805. Internal data logging capabilities can also be provided for to record selected full waveform and setup information associated with each test.

Figure 9:
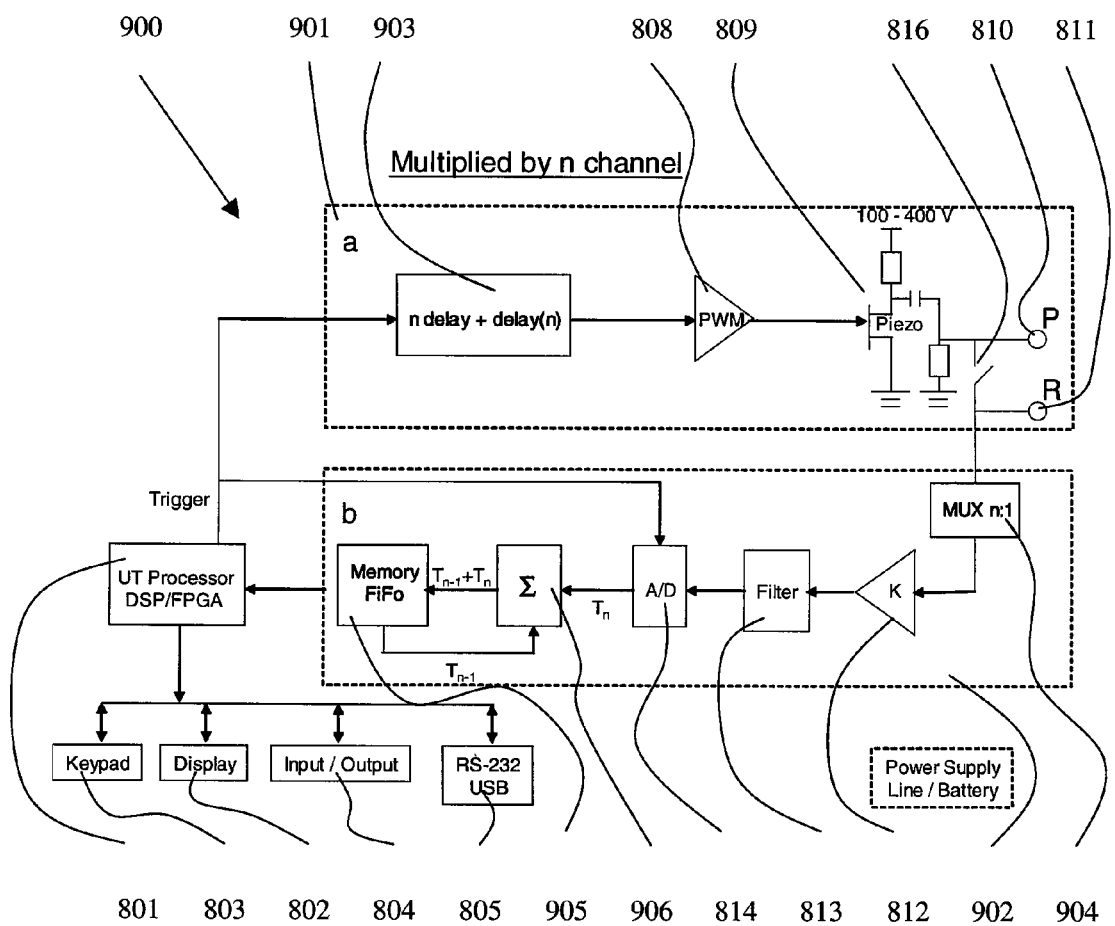
FIG. 9 is a block diagram of a non-restrictive, illustrative embodiment of the flaw detector imaging apparatus according to the present invention.

FIG. 9 illustrates a non-restrictive illustrative embodiment 900 of the hand-held flaw detector 301 of FIG. 3. The embodiment 900 of FIG. 9 comprises many elements of the embodiment 800 of FIG. 8; the elements of the embodiment 900 of FIG. 9 corresponding to elements of the embodiment 800 of FIG. 8 are identified by the same reference numerals and will not be further described in the present specification.

As illustrated in FIG. 9, each channel 806 is divided into a trigger channel 901 and a receiver channel 902. More specifically, the hand-held flaw detector 900 comprises n identical and parallel trigger channels 901 respectively associated to the ultrasonic transducers 307 (FIG. 3) and a single receiver channel 902.

Figure 10:
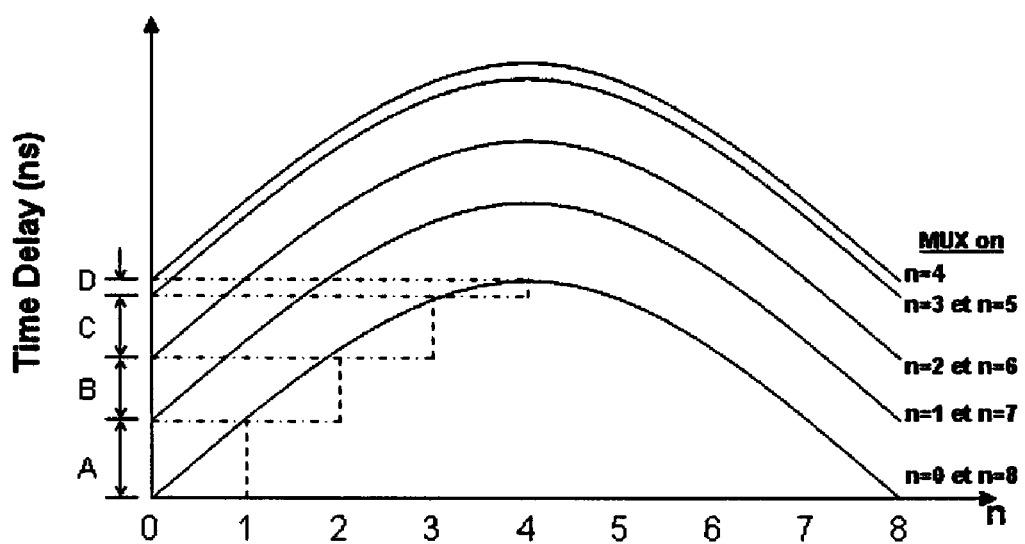
FIG. 10 is a graph illustrating focal law profiles for a non-restrictive illustrative compact embodiment of the flaw detector imaging apparatus in accordance with the present invention.

In each trigger channel 901, delay circuit 807 is replaced by a delay circuit 903. In this delay circuit 903, the delay is determined from equivalent or modified law delay profiles calculated as illustrated in FIG. 10. This concept is expressed by: n delay+delay(n). More specifically, in an example comprising a number of nine (9) ultrasonic transducers 307 in the phase-array probe 305, for channel n=0, the delay introduced by circuit 903 is equal to the delay (delay (n)) calculated in accordance with the corresponding law delay profile in circuit 807. For channel n=1, the delay introduced by circuit 903 is equal to the delay (delay (n)) calculated in accordance with the corresponding law delay profile in circuit 807 plus a delay A (n delay). For channel n=2, the delay introduced by circuit 903 is equal to the delay (delay (n)) calculated in accordance with the corresponding law delay profile in circuit 807 plus a delay A+B (n delay). For channel n=3, the delay introduced by circuit 903 is equal to the delay (delay (n)) calculated in accordance with the corresponding law delay profile in circuit 807 plus a delay A+B+C (n delay). For channel n=4, the delay introduced by circuit 903 is equal to the delay (delay (n)) calculated in accordance with the corresponding law delay profile in circuit 807 plus a delay A+B+C+D (n delay). For channel n=5, the delay introduced by circuit 903 is equal to the delay (delay (n)) calculated in accordance with the corresponding law delay profile in circuit 807 plus a delay A+B+C+D-D=A+B+C (n delay). For channel n=6, the delay introduced by circuit 903 is equal to the delay (delay (n)) calculated in accordance with the corresponding law delay profile in circuit 807 plus a delay A+B+C+D-D-C=A+B (n delay). For channel n=7, the delay introduced by circuit 903 is equal to the delay (delay (n)) calculated in accordance with the corresponding law delay profile in circuit 807 plus a delay A+B+C+D-D-C-B=A (n delay). For channel n=8, the delay introduced by circuit 903 is equal to the delay (delay (n)) calculated in accordance with the corresponding law delay profile in circuit 807 plus a delay A+B+C+D-D-C-B-A=0 (n delay).

Therefore, the trigger channels 901 are capable of exciting the ultrasonic transducers 307 of the phase-array probe 305 at n respective, consecutive trigger times delayed with respect to each other in accordance with the modified focal law profiles of FIG. 10, in order to send focused and/or steered ultrasonic beams. At each separate trigger, only one ultrasonic echo is collected by the receiver channel 902 and supplied to a FIFO memory 905 through a multiplexer 904, the amplifier 812, the filter 813, the analog-to-digital converter 814 and an adder 906. As illustrated in FIG. 9, each new channel signal $T_n$ supplied to the adder 906 is added to the summed prior channel signals $T_{n-1}$. Once the n time-multiplexed receiver channel signals have been collected through the multiplexer 904, added together through the adder 906 and stored in the FIFO memory, the sum of these signals is sent to the ultrasonic processor 801 for generating and displaying the S-Scan image on the display unit 802 as described in the foregoing description.

Again, the law delay profiles used in the receiver channel 902 are formed by delays which are added to the delay profiles calculated for the trigger channels 901 during excitation of the n ultrasonic transducers 307 of the phase-array probe 305. Again, these equivalent or modified law delay profiles are calculated as illustrated in FIG. 10. As indicated hereinabove, this concept can be expressed as <<n delay+delay(n)>>. More specifically, in an example comprising a number of nine (9) ultrasonic transducers 307 in the phase-array probe 305, when the multiplexer value is n=0, the law profile delay is equal to the delay (delay (n)) calculated in accordance with the corresponding law delay profile in circuit 807. When the multiplexer value is n=1, the law profile delay is equal to the delay (delay (n)) calculated in accordance with the corresponding law delay profile in circuit 807 plus a delay A (n delay). When the multiplexer value is n=2, the law profile delay is equal to the delay (delay (n)) calculated in accordance with the corresponding law delay profile in circuit 807 plus a delay A+B (n delay). When the multiplexer value is n=3, the law profile delay is equal to the delay (delay (n)) calculated in accordance with the corresponding law delay profile in circuit 807 plus a delay A+B+C (n delay). When the multiplexer value is n=4, the law profile delay is equal to the delay (delay (n)) calculated in accordance with the corresponding law delay profile in circuit 807 plus a delay A+B+C+D (n delay). When the multiplexer value is n=5, the law profile delay is equal to the delay (delay (n)) calculated in accordance with the corresponding law delay profile in circuit 807 plus a delay A+B+C+D-D=A+B+C (n delay). When the multiplexer value is n=6, the law profile delay is equal to the delay (delay (n)) calculated in accordance with the corresponding law delay profile in circuit 807 plus a delay A+B+C+D-D-C=A+B (n delay). When the multiplexer value is n=7, the law profile delay is equal to the delay (delay (n)) calculated in accordance with the corresponding law delay profile in circuit 807 plus a delay A+B+C+D-D-C-B=A (n delay). When the multiplexer value is n=8, the law profile delay is equal to the delay (delay (n)) calculated in accordance with the corresponding law delay profile in circuit 807 plus a delay A+B+C+D-D-C-B-A=0 (n delay).

Figure 11:
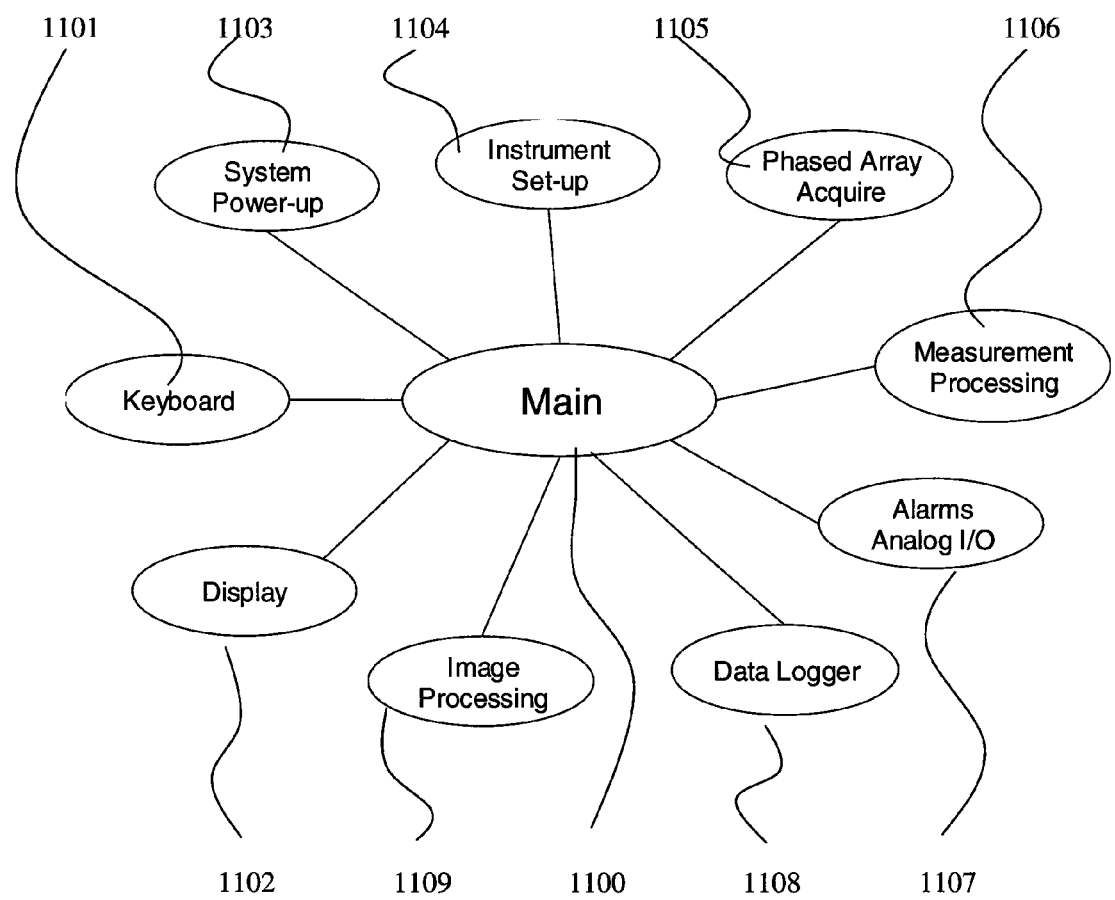
FIG. 11 is a schematic diagram of a software process for the flaw detector imaging apparatus.

FIG. 11 is a schematic diagram of the software structure of the hand-held flaw detector imaging apparatus.

As illustrated in FIG. 11, the software structure comprises a main program 1100 accessible and configurable through a keyboard 1101 and display unit 1102. Connected to the main program 1100 are system power-up routine 1103, instrument set-up routine 1104, phase-array acquisition routine 1105, measurement processing routine 1106, alarms analog input/output routine 1107, data logger routine 1108, image processing routine 1109. Such a structure is well known to those of ordinary skill in the art and accordingly will not be further described in the present specification.

Figure 12:
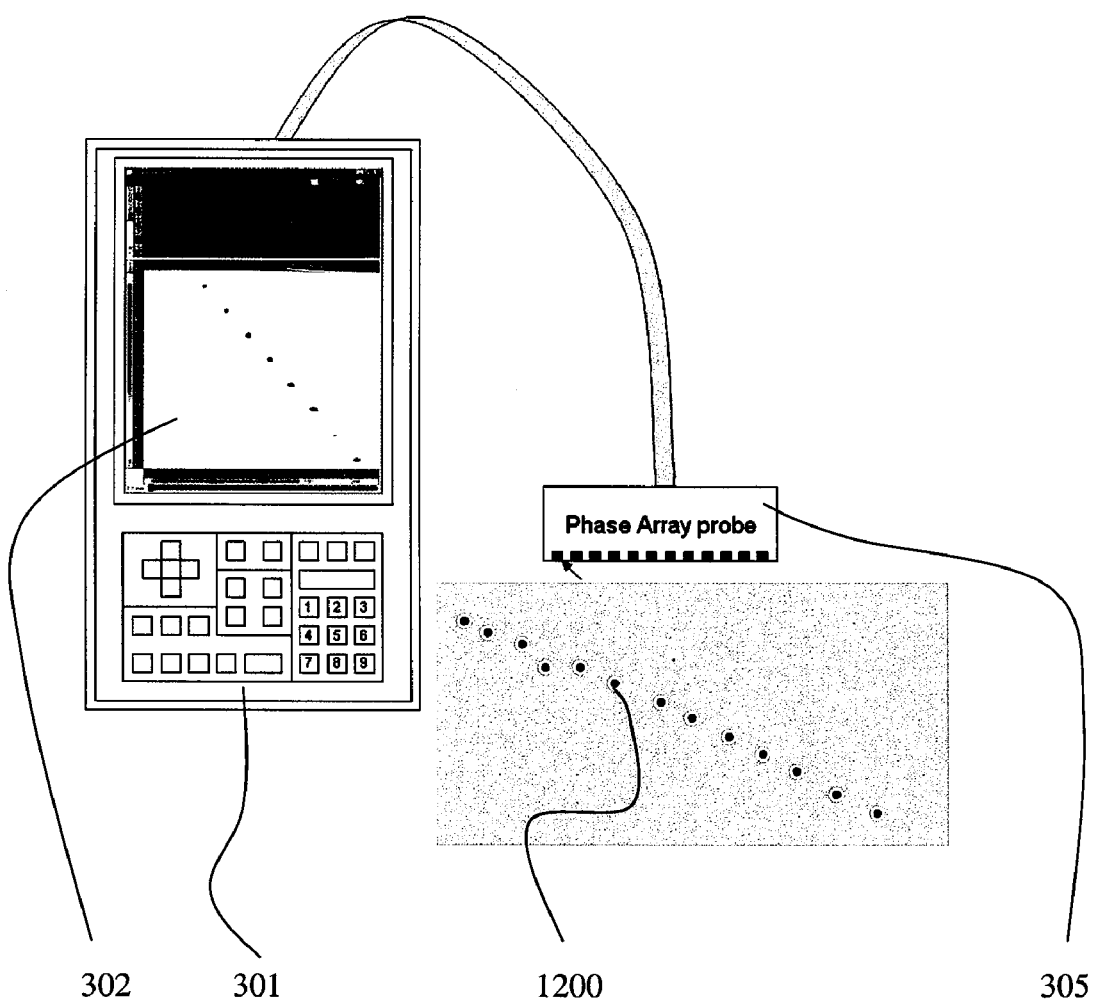
FIG. 12 is a schematic representation of user display panel of the flaw detector imaging apparatus including a waveform display and a reconstructed sectorial S-Scan display image.
Figure 13:
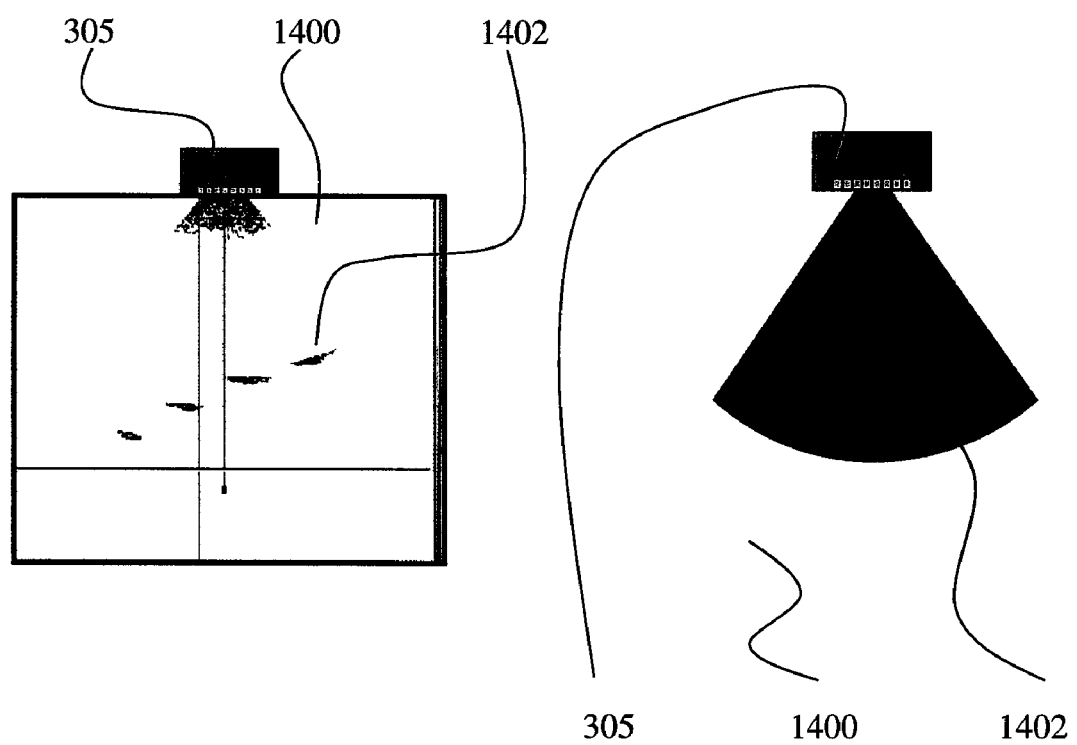
FIG. 13 is a schematic representation of sectorial scanning (S-Scan) principle with a phase-array probe showing detection of side drilled holes in a block or test specimen.

FIG. 12 depicts defect detection and characterization. More specifically, FIG. 12 depicts how the flaw detector 301 can display on the display 302 an image showing not only the nature of the flaws such as 1200 but also the position of these flaws. While probing with the phase-array probe 305, the electronic scanning and S-Scan display takes only a fraction of a second. Once an indication of the possible presence of a defect has been detected, the scanning can be adjusted to evaluate a smaller region around the possible defect location. For example, the phase-array probe 305 can be used to probe, for example, an aluminium structure 1400 containing side drilled holes 1402 as shown in FIG. 13. A number of consecutive sequences of focal law profiles as described in the foregoing description can be used to interrogate much smaller volumes, thereby allowing investigation using additional angles and finer increments Although this is not illustrated, the phase-array probe 305 can be provided with integrated circuitry for automatic configuration. This circuitry allows the phase-array probe 305 to store standard law delay profiles and the original configuration of the array.

Advantages of the illustrative embodiments of the hand-held flaw detector imaging apparatus comprise, amongst others, improvement of the conventional flaw detector concept in association with imaging of flaws in material for rapid interpretation of the results. Moreover, using the hand-held flaw detector imaging apparatus coupled to the phase-array scanning concept permits easy flaw characterization. Ultrasonic beam focusing and steering provides great flexibility in scanned patterns, contributing to improve reliability and discover hidden flaws.

Amongst other advantages, the above-described, non-restrictive illustrative embodiments according to the present invention:

are particularly useful for rapid real-time detection and visualization of flaws found in engineering materials used for industrial, aerospace and power generation applications;

improve the conventional flaw detector concept and the way in which materials are evaluated for flaws by enabling actual visualization of flaws and rapid interpretation of the results from material evaluation, and by introducing a hand-held flaw detector, which uses a phase-array probe to produce an image at a single location by focusing and/or steering the ultrasonic beam;

reduce hardware complexity and cost of the flaw detector imaging apparatus by using a multi-trigger and single receiver channel configuration reducing the volume of the electronic components and the consumed energy of the hand-held apparatus;

provide an ultrasonic phase-array probe which is programmable for material imaging and evaluation;

automate flaw detection using the S-Scan display of the flaw detector imaging apparatus to provide real-time flaw detection capabilities and reduce operator intervention for data interpretation compared to, for example, A-Scan interpretation;

improve portability of the hand-held flaw detector imaging apparatus; the hand-held flaw detector imaging apparatus is battery powered with lightweight and presents a compact integrated design attached to an ultrasonic phase-array probe.

Figure 14:
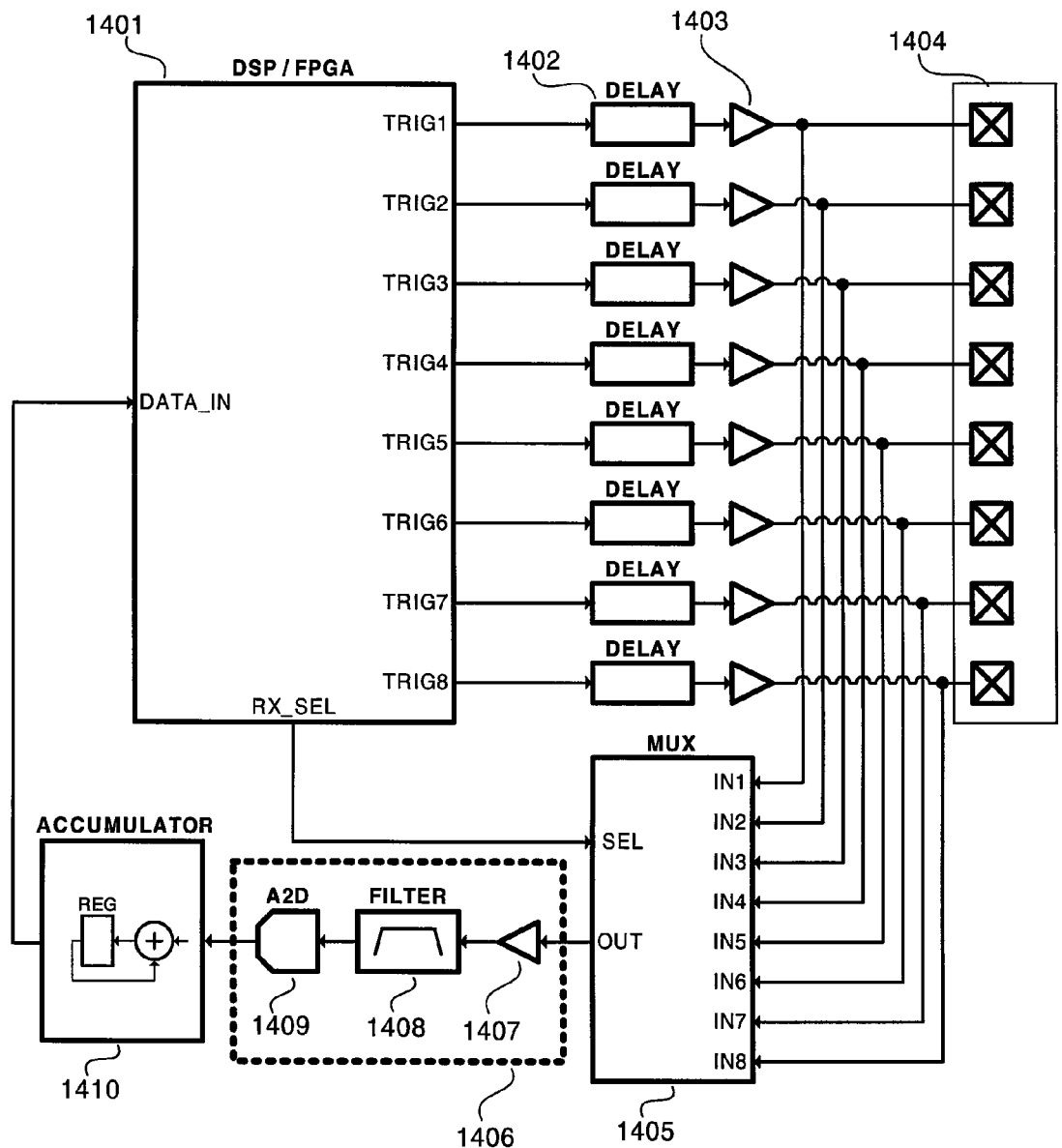
FIG. 14 is a schematic diagram of a typical non-destructive inspection architecture suitable for use with the minimal receiver channel acquisition algorithm of the present disclosure.

FIG. 14 illustrates an exemplary non-destructive inspection (NDI) instrument architecture which is well suited to make use of the minimal receiver acquisition algorithm of the present disclosure. A digital signal processing element (or, alternatively an FPGA element) 1401 provides a plurality of trigger signals to an array of transducer elements 1404 through delay elements 1402 and buffer elements 1403. Said delay elements 1402 and buffer elements 1403 provide means to delay and shape (pulse width or voltage adjustment, for example) each of the trigger signals.

A multiplexer element 1405 is responsive to return signals from each of the elements 1404 in the transducer array. The digital signal processing element 1401 has means to control the multiplexer element 1405 such as to provide the return signal from any single transducer of elements 1404 to the receiver channel 1406. The selected return signal is then provided to an analog to digital converter element 1409 through buffer element 1407 and filter element 1408, providing means for shaping and filtering said return signal. After digitization, the selected return signal is stored in an accumulator element 1410, which has means to provide waveform data resulting form the accumulation of a plurality of signals to the digital signal processing element 1401.

It should be noted that while the receiver channel 1406 in FIG. 14 is depicted in a particular arrangement, the methods of the present disclosure are not limited in this regard. Indeed, receiver channels used in NDI instruments are well known to those skilled in the art, and it will obvious to those skilled in the art that filtering and shaping of an ultrasonic signal received from a transducer, for example, can be readily performed after digitization of said signal. As such, the specific layout and architecture of the receiver channel 1406 should not be viewed as specific to the algorithm of the present disclosure.

It also should be noted that while NDI instrument architecture depicted in FIG. 14 shows only one MUX 1405 and one receiver channel 1406, the methods of the present disclosure are not limited in this regard. Indeed, as will be shown below in the detailed discussion of the minimal receiver acquisition algorithm of the present disclosure, the methods of said disclosure can be readily applied to an NDI instrument architecture comprising a plurality of receiver channels 1406.

Figure 15:
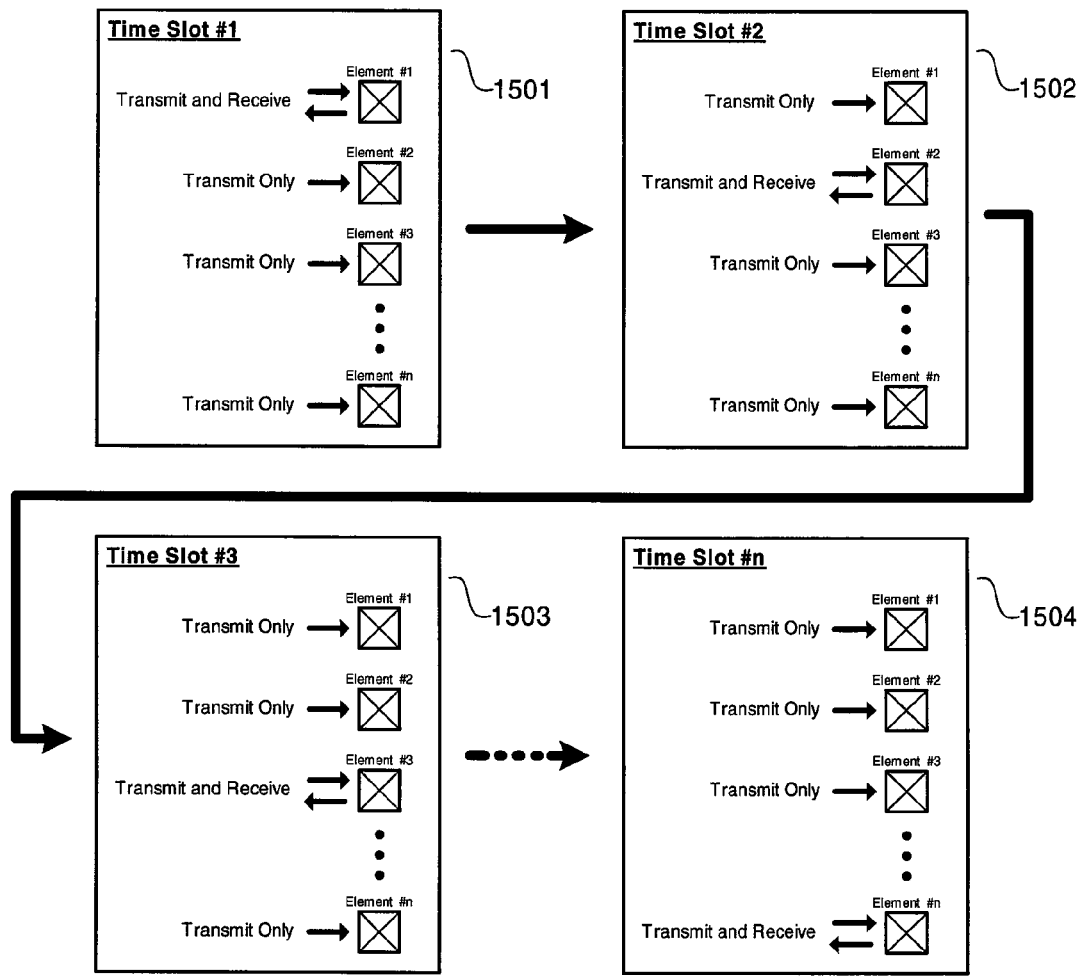
FIG. 15 is a timing slot diagram of the minimal receiver channel acquisition algorithm of the present disclosure.

FIG. 15 is a timing sequence diagram illustrating the minimal receiver acquisition system of the present disclosure. The algorithm takes advantage of the principle that return signals within an ultrasonic NDI inspection are highly repeatable (given a probe in a fixed position, fired with a single set of focal laws). As such, multiple firing sequences can be used to acquire a complete ultrasonic image of a material under inspection while using less receiver channels than elements within the transducer array.

FIG. 15 depicts a plurality of time slots during which time a different transducer is coupled to a receiver channel. Time slot 1501 depicts a first time slot, wherein all elements are energized and only the first element is coupled to the receiver channel. Time slot 1502 depicts a second time slot, wherein all elements are energized and only the second element is coupled to the receiver channel. Time slot 1503 depicts a third time slot, wherein all elements are energized and only the third element is coupled to the receiver channel. Time slot 1504 depicts a final time slot, wherein all elements are energized and only the last (or "nth") element is coupled to the receiver channel.

During each time slot, all of the transducer elements are fired according to the desired set of focal laws. In the preferred embodiment of the present disclosure, exactly one transducer element is coupled to a receiver channel during each time slot, and the return signal sensed by said transducer element is provided to an accumulator (1410 in FIG. 14) through a receiver channel (1406 in FIG. 14). In each of the subsequent time slots, a different transducer element is coupled to the receiver channel such that all of the return signals sensed within the inspection operation are combined in the accumulator. In this way, a multi-element NDI dataset can be acquired via a superposition process, thereby significantly reducing the number of receiver channels required.

It should be noted that while the preferred embodiment of the present disclosure makes use of a single receiver channel, the methods of the present disclosure are not limited in this regard. Indeed, a plurality of receiver channels could be used thereby limiting the number of time slots required to execute the algorithm.

Although the present invention has been described in the foregoing description with reference to non-restrictive illustrative embodiments thereof, these embodiments can be modified at will, within the scope of the appended claims without departing from the spirit and nature of the present invention.

What is claimed is:

1. A method of ultrasonic inspection for use with an ultrasonic imaging system comprising a pulse generating array including a plurality of transducer elements and a single receiver channel, the method comprising:

coupling a first element of the array to the single receiver channel;

energizing the transducer elements within said array according to a set of focal laws;

processing an echo signal sensed by said first transducer element through said single receiver channel;

providing a digitized value representative of said echo signal;

summing said digitized value in an accumulator;

coupling a second element of said array to said single receiver channel;

energizing the transducer elements and obtaining a respective digitized value corresponding to said second element;

summing the digitized value of the second element in said accumulator; and repeating said process steps to provide a cumulative sum value for a predetermined number of the transducer elements of said array.

2. The method of claim 1, wherein said processing is carried out for all of the transducer elements in said array.

3. The method of claim 1, including processing the echo signal relative to all of the transducer elements to obtain each respective digitized value.

4. The method of claim 1, in which said accumulator comprises:
 a memory block containing a previously stored value; and
 a summing block which sums said digitized values with said previously stored value and loads a new value resulting from the summation operation into said memory block.

5. The method of claim 1, including first setting the accumulator to an initial value.

6. A method of ultrasonic inspection for use with an ultrasonic imaging system comprising a pulse generating array including a plurality of transducer elements and a plurality of receiver channels, the method comprising:
 coupling a first group of elements of the array to the receiver channels;
 energizing the first group of said array according to a set of focal laws;
 processing echo signals sensed by said first group of transducer elements through said receiver channels;
 obtaining a respective digitized value representative for each of said echo signals;
 summing said digitized values into an accumulator;
 coupling a second group of transducer elements of said array to said receiver channels;
 energizing said array and obtaining a respective digitized value for the second group;
 summing the respective digitized values of the second group in said accumulator; and
 repeating said process steps to provide a cumulative sum value for a predetermined number of groups of the transducer elements of said array.

7. The method of claim 6, wherein the number of elements in said first group equals the number of receiver channels.

8. The method of claim 6, in which the number elements in the second group equals the number of transducer elements in the first group.

9. The method of claim 6, wherein said processing is carried out for a sufficient number of said groups to include all of the transducer elements in said array.

10. The method of claim 6, in which said accumulator comprises:
 a memory block containing a previously stored value; and
 a summing block which sums said digitized values with previously stored values and loads new values resulting from the summation operation into said memory block.

* * * * *